United States Patent [19]

Köllensperger et al.

[11] 4,179,442
[45] Dec. 18, 1979

[54] 4-(ALPHA-HYDROXY-ISOPROPYL)-5-PHENYL-OXAZOLIDIN-2-ONE

[76] Inventors: Friedrich-Gero Köllensperger, Galvanistrasse 20, Linz, Austria; York Hartleben, Kleiner Ring 7, 2081 Heist, Fed. Rep. of Germany; Rolf Kretzschmar, An der Dune 2, 2082 Moorrege, Fed. Rep. of Germany; Bernhard Neteler, Hüntestrasse 13, 29 Oldenburg, Fed. Rep. of Germany

[21] Appl. No.: 932,102

[22] Filed: Aug. 9, 1978

Related U.S. Application Data

[62] Division of Ser. No. 718,610, Aug. 30, 1976, Pat. No. 4,139,538.

[30] Foreign Application Priority Data

Aug. 29, 1975 [DE] Fed. Rep. of Germany ....... 2538424

[51] Int. Cl.² .......................................... C07D 263/24
[52] U.S. Cl. ..................................... 548/232; 424/272
[58] Field of Search ..................................... 260/307 C

[56] References Cited

U.S. PATENT DOCUMENTS

| 2,824,878 | 2/1958 | Alberti et al. | 260/307 C |
| 3,133,932 | 5/1964 | Horn et al. | 260/307 C |
| 4,139,538 | 2/1979 | Köllensperger et al. | 260/307 C |

Primary Examiner—Jose Tovar
Attorney, Agent, or Firm—Pearne, Gordon, Sessions

[57] ABSTRACT

The present invention is related to new oxazolidin-2-one derivatives having the general formula

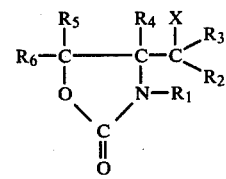

The invention is further related to a process for the treatment of somnipathy and tension conditions as well as epilepsy conditions in humans by administering a compound of the above general formula to a human suffering from such conditions.

1 Claim, No Drawings

4-(ALPHA-HYDROXY-ISOPROPYL)-5-PHENYL-OXAZOLIDIN-2-ONE

This is a division of application Ser. No. 718,610, filed Aug. 30, 1976, now U.S. Pat. No. 4,139,538, issued Feb. 13, 1979.

This invention relates to new oxazolidinones corresponding to the general formula

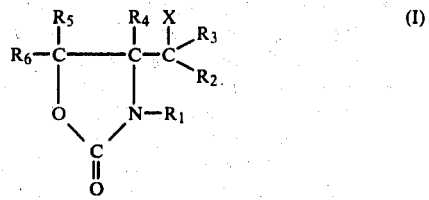

in which X represents hydroxy, chlorine or bromine, $R_1$ represents hydrogen, straight-chain or branched, saturated or unsaturated alkyl radicals with 1 to 4 carbon atoms or benzyl, $R_2$ represents hydrogen, straight-chain or branched, saturated or unsaturated alkyl radicals with 1 to 4 carbon atoms, the unsubstituted phenyl radical or the phenyl radical substituted once or twice by halogen, lower alkyl with 1 to 4 carbon atoms, lower alkoxy with 1 to 4 carbon atoms and/or trifluoromethyl or the unsubstituted benzyl radical or the benzyl radical substituted once or twice by halogen, lower alkyl with 1 to 4 carbon atoms, lower alkoxy with 1 to 4 carbon atoms and/or trifluoromethyl, $R_3$ represents hydrogen, a straight-chain or branched, saturated or unsaturated alkyl radical with 1 to 4 carbon atoms, the unsubstituted phenyl radical or the phenyl radical substituted once or twice by halogen, lower alkyl with 1 to 4 carbon atoms, lower alkoxy with 1 to 4 carbon atoms and/or trifluoromethyl or the unsubstituted benzyl radical or the benzyl radical substituted once or twice by halogen, lower alkyl with 1 to 4 carbon atoms, lower alkoxy with 1 to 4 carbon atoms and/or trifluoromethyl, $R_4$ represents hydrogen, a straight-chain or branched, saturated or unsaturated alkyl radical with 1 to 4 carbon atoms or the phenyl radical, $R_5$ represents hydrogen, an alkyl radical with 1 to 4 carbon atoms or the phenyl radical and $R_6$ represents hydrogen, an alkyl radical with 1 to 4 carbon atoms or the phenyl radical, or $R_5$ and $R_6$ together represent an alkylene radical with 4 to 6 carbon atoms in the chain.

Preferred compounds of formula I are those in which X represents hydroxy, chlorine or bromine, $R_1$ represents hydrogen, lower alkyl with 1 to 4 carbon atoms, allyl or benzyl, $R_2$ represents hydrogen, lower alkyl with 1 to 4 carbon atoms, allyl, unsubstituted phenyl or phenyl monosubstituted by chlorine, $R_3$ represents hydrogen, lower alkyl with 1 to 4 carbon atoms, allyl, unsubstituted phenyl or phenyl monosubstituted by a chlorine atom, $R_4$ represents hydrogen, $R_5$ represents hydrogen, lower alkyl with 1 to 4 carbon atoms or phenyl and $R_6$ represents hydrogen.

Particularly favourable properties are shown by compounds of formula I in which X represents hydroxy, chlorine or bromine, $R_1$ represents hydrogen or methyl, $R_2$ represents hydrogen, methyl, phenyl, p-chlorophenyl or allyl, $R_3$ represents hydrogen, methyl or allyl, $R_4$ represents hydrogen, $R_5$ represents hydrogen, methyl or phenyl and $R_6$ represents hydrogen. Accordingly, these compounds are particularly preferred.

The compounds according to the present invention may be produced by methods known per se. In such processes, a compound corresponding to the general formula

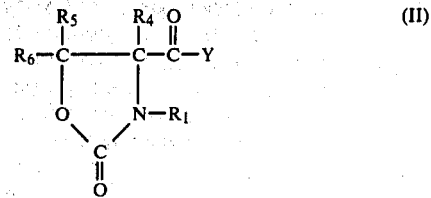

in which Y represents a lower, straight-chain alkoxy radical with upt to 2 carbon atoms, hydrogen, straight-chain or branched, saturated or unsaturated alkyl radical or the phenyl radical substituted once or twice by halogen, lower alkyl with 1 to 4 carbon atoms, lower alkoxy with 1 to 4 carbon atoms and/or trifluoromethyl or the unsubstituted benzyl radical or the benzyl radical substituted once or twice by halogen, lower alkyl with 1 to 4 carbon atoms, lower alkoxy with 1 to 4 carbon atoms and/or trifluoromethyl and $R_1$, $R_4$, $R_5$ and $R_6$ are as defined above, is hydrogenated with a metal hydride, for example lithium aluminium hydride or sodium borohydride, or is reacted with an organometallic compound corresponding to the general formula III

$$R_7-Mg-Hal \qquad (III)$$

in which $R_7$ is a straight-chain or branched, saturated or unsaturated alkyl group with 1 to 4 carbon atoms, the unsubstituted phenyl group or the phenyl group substituted once or twice by halogen, lower alkyl with 1 to 4 carbon atoms, lower alkoxy with 1 to 4 carbon atoms and/or trifluoromethyl, or the unsubstituted benzyl group or the benzyl group substituted once or twice by halogen, lower alkyl with 1 to 4 carbon atoms, lower alkoxy with 1 to 4 carbon atoms and/or trifluoromethyl, and Hal is a halogen atom, under the conditions of a Grignard reaction, the compound obtained corresponding to general formula I, in which X is the hydroxyl group and $R_1$, $R_2$, $R_3$, $R_4$, $R_5$ and $R_6$ are as defined above, is, if desired, reacted with a chlorinated or brominating agent, for example with thionyl chloride, and X thus converted into a chlorine or, respectively, bromine atom.

The use of metal hydrides results in the formation of compounds of formula I in which $R_2$ represents hydrogen and $R_1$, $R_3$, $R_4$, $R_5$ and $R_6$ are as defined above. Application of the Grignard reaction results in the formation of compounds of formula I in which $R_2$ and $R_3$ have the same meanings as defined above except for hydrogen.

Compounds corresponding to general formula II are known from the literature (cf. for example G. F. Hennion and F. X. O'Shea, J.org. Chem. 23, (1958) 662–664; M. E. Dyen and D. Swern, Chem.Rev. 67, (1967) 197–246).

The oxazolidinones of general formula I have valuable pharmacodynamic properties. They show outstanding anticonvulsive, tranquillizing and sleep-inducing properties and have a relaxing effect upon the central muscle system, and are therefore suitable for the treatment of humans suffering from somnipathy, tensions, muscular tensions, and for the treatment of diseases causing fits such as diseases of the petit mal type or myoclonus epilepsy and akinetic epilepsy.

Thus, when administered orally and intraperitoneally in suitable doses to standard laboratory test animals, such as albino mice (NMRI strain, breeders Invanovas, Kissleg) and albino rats (Sprague Dawley strain, breeders Invanovas, Kissleg), the compounds according to the invention develop a safe protective effect against tonic extensor cramp in the maximum electric shock test (MES) and also a safe protective effect against clonoc sonvulsions initiated by the subcutaneous injection of 70 mg/kg of pentetrazole (minimum pentetrazole shock test=min PS). The toxicity of the compounds is very low. With suitable substitution, the compounds corresponding to general formula I, especially those of Examples 4, 5, 37, 54 and 67, are superior to a few conventional antiepileptics, such as trimethadione and dipropyl acetate, in the anticonvulsive test models referred to.

In addition, the compounds according to the invention also differ in their effect from conventional antiepileptics of the hydantoin type, such as diphenyl hydantoin for example, insofar as they clearly inhibit clonic cramp where as hydantoins have no effect on clonic cramp.

In addition to their anticonvulsive activity, the compounds according to the invention have a relaxing effect upon the central muscle system which is reflected in paralysis of the test animals, causing them to lie on their sides. In addition, they enhance the effect of narcotics, for example the period of sleep following the intravenous administration of 70 mg/kg of sodium hexobarbitone. With suitable substitution, compounds corresponding to general formula I, especially those of Examples 38, 43, 54 and 64, are distinctly more effective in prolonging sleep and relaxing the muscle system than known hypnotics and tranquillizers, such as for example chlorzoxazone and meprobamate.

The effect of some of the compounds according to the invention in animal experiments is compared in Table 1 below with the effect of known antiepileptics and tranquillizers.

Table 1a

Formula I

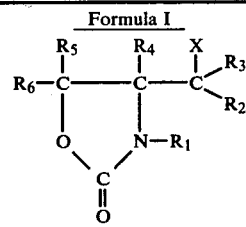

| Example No. | X  | $R_1$        | $R_2$           | $R_3$           | $R_4$  | $R_5$    | $R_6$    |
|-------------|----|--------------|-----------------|-----------------|--------|----------|----------|
| 6           | OH | —H           | —H              | —H              | —$CH_3$ | —$CH_3$  | —$C_6H_5$ |
| 34          | OH | —H           | —$CH_2CH=CH_2$  | —$CH_2CH=CH_2$  | —H     | —$CH_3$  | —H       |
| 37          | OH | —H           | —$CH_3$         | —$CH_3$         | —H     | —$C_6H_5$ | —H       |
| 38          | OH | 3            | —$CH_3$         | —$CH_3$         | —H     | —$C_6H_5$ | —H       |
| 39          | OH | —$CH_2CH=CH_2$ | —$CH_3$       | —$CH_3$         | —H     | —$C_6H_5$ | —H       |
| 40          | OH | —H           | —$C_2H_5$       | —$C_2H_5$       | —H     | —$C_6H_5$ | —H       |
| 41          | OH | —H           | n-$C_3H_7$      | n-$C_3H_7$—     | —H     | —$C_6H_5$ | —H       |
| 43          | OH | —H           | —$CH_2CH=CH_2$  | —$CH_2CH=CH_2$  | —H     | —$C_6H_5$ | —H       |
| 45          | OH | —H           | n-$C_3H_7$—     | n-$C_3H_7$—     | —H     | —H       | —H       |
| 4           | OH | —H           | —H              | —$C_6H_4$p-Cl   | —H     | —H       | —H       |
| 49          | OH | —H           | —$C_6H_4$-m-Cl  | —$C_6H_5$       | —H     | —H       | —H       |
| 54          | OH | —H           | —$C_2H_5$       | —$C_6H_5$       | —H     | —H       | —H       |
| 58          | OH | —H           | —$CH_2$—$CH=CH_2$ | —$C_6H_5$     | —H     | —H       | —H       |
| 5           | OH | —H           | —$CH_3$         | —H              | —H     | —$C_6H_5$ | —H       |
| 18          | OH | —H           | —$C_2H_5$       | —$C_6H_5$       | —H     | —$CH_3$  | —H       |
| 59          | OH | —H           | —$CH_3$         | —$C_6H_4$—p-Cl  | —H     | —H       | —H       |
| 60          | OH | —H           | —$C_2H_5$       | —$C_6H_4$—p-Cl  | —H     | —H       | —H       |
| 64          | OH | —$CH_3$      | —$C_2H_5$       | —$C_6H_5$       | —H     | —H       | —H       |
| 65          | OH | —H           | n-$C_3H_7$      | —$C_6H_5$       | —H     | —H       | —H       |
| 67          | Cl | —H           | —H              | —H              | —H     | —$C_6H_5$ | —$CH_3$  |
| 72          | Cl | —H           | —H              | —H              | —H     | —$C_6H_5$ | —H       |
| 73          | Br | —H           | —H              | —H              | —H     | —$C_6H_5$ | —H       |

Table 1b

Formula I

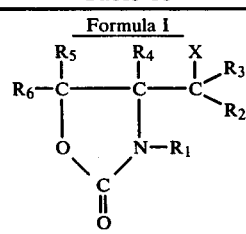

| Example No. | Anticonvulsive activity | | Prolongation of narcosis[3] $ED_{200}$ | Paralysis[4] $ED_{50}$ | Acute toxicity $LD_{50}$ |
|---|---|---|---|---|---|
| | $MES^{(1)}$ $ED_{50}$ | Min $PS^{(2)}$ $ED_{50}$ | | | |
| | | | mg/kg p.o. (mice) | | |
| 6 | 165 | —* | 1000 | 1000 | >1000 |

Table 1b-continued

Formula I

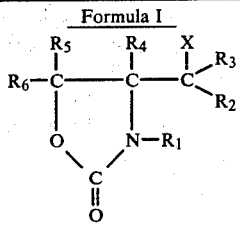

| Example No. | Anticonvulsive activity MES[1] $ED_{50}$ | Min PS[2] $ED_{50}$ | Prolongation of narcosis[3] $ED_{200}$ | Paralysis[4] $ED_{50}$ | Acute toxicity $LD_{50}$ |
|---|---|---|---|---|---|
| | mg/kg p.o. (mice) | | | | |
| 34 | 150 | —* | 90 | 1000 | >1000 |
| 37 | 59 | 130 | 650 | 1000 | >1000 |
| 38 | 165 | 640 | 115 | 464 | >1000 |
| 39 | 145 | —* | 130 | —** | 1000 |
| 40 | 75 | 430 | 165 | 1000 | >1000 |
| 41 | 147 | —* | 65 | —** | >1000 |
| 43 | 25 | —* | 15 | 225 | 1000 |
| 45 | 120 | 430 | 210 | 1000 | >1000 |
| 4 | 125 | 140 | 160 | —** | >1000 |
| 49 | 200 | —* | 90 | —** | >1000 |
| 54 | 115 | 85 | 50 | 800 | >1000 |
| 58 | 200 | 300 | 300 | 1000 | >1000 |
| 5 | 75 | 150 | 510 | —** | >1000 |
| 18 | 200 | 200 | 450 | —** | >1000 |
| 59 | 165 | —* | 110 | —** | >1000 |
| 60 | 175 | —* | 70 | 1000 | >1000 |
| 64 | 300 | —* | 110 | 650 | 800 |
| 65 | 170 | 175 | 155 | —** | >1000 |
| 67 | 93 | 55 | 210 | 1000 | >1000 |
| 72 | 75 | 540 | 115 | —** | >1000 |
| 73 | 65 | 430 | 420 | —** | >1000 |
| Na-phenocarbital | 11 | 30 | 30 | 150 | 320 |
| Trimethadione | 450 | 240 | 660 | —** | >1000 |
| Dipropylacetate | 185 | 450 | 355 | 1000 | >1000 |
| Diphenylhydantoin | 10 | ineffectual | 50 | no paralytic effect | 360 |
| Meprobamate | 115 | 150 | 150 | 800 | 1000 |
| Chlorozoxazone | 110 | 540 | —* | 350 | 650 |

Key to Table 1b
[1] Effect against maximum electric shock in mice 60 minutes after p.o. administration (stimulus data: ear electrodes, 19 mA, 4.64 msec.) $ED_{50}$ = protection against tonic extensor cramp in 50% of the animals
[2] Effect against clonic pentetrazole-induced cramp in mice 70 mg/kg of pentetrazole s.c., 60 minutes after p.o. administration of the substances $ED_{50}$ = protection against clonic cramp in 50% of the animals
[3] Sodium hexobarbitone, i.v. injection of 70 mg/kg, 60 minutes after p.o. administration of the substances $ED_{200}$ = extension of the narcosis period to 200%
[4] Loss of the postural and balancing reflexes (lying down) in 50% of the animals ($ED_{50}$)
[5] Acute toxicity over 7 days' post observation, maximum test dose = 1000 mg/kg
*No effect up to a dose of 464 mg/kg
**No effect up to a dose of 1000 mg/kg Accordingly, the present invention also relates to pharmaceutical preparations with an anticonvulsive effect on the one hand and with a sedative, sleep-including and tranquillizing effect on the other hand, containing one or more oxazolidinones of general formula I as active principle.

Pharmaceutical preparations such as these may be produced by methods known per se to the expert in accordance with the particular form of administration required. They generally contain at least one active compound according to the invention in admixture with non-toxic, inert, solid or liquid carriers and/or excipients which are suitable for systemic use and which are normally used in preparations such as these.

Preparations for parenteral administration, for example for the treatment of sleeplessness or cramp, may be formulated in known manner by introducing an effective quantity of a compound of formula I into a standard inert carrier, suspension or solvent medium together with other additives, such as dispersants, wetting agents, buffers and other ingredients.

The preparations suitable for parenteral or oral administration may generally contain from 1 to 90% by weight, better still from 3 to 40% by weight, of active principle in conjunction with an inert carrier.

For treating an adult or juvenile human, each dose of the active constituent of a compound of general formula I administered in the form of a suitable pharmaceutical preparation such as a tablet, dragee, capsule, suspension or solution amounts to between about 10 and 500 mg. with a daily dose ranging from 30 to 1500 mg. This treatment may be effected for 1 to several days ranging up to even one month or more. These doses apply both to the treatment of epilepsy of the Petit mal type or of myoclonus or alkinetic epilepsy and to the treatment of for instance sleeplessness or states of superactivity.

The invention is further illustrated by the following Examples:

EXAMPLES ILLUSTRATING THE REACTION WITH METAL HYDRIDES

(1) 4-Hydroxymethyl oxazolidin-2-one 7.54 g (0.199 mole) of sodium borohydride are added in portions over a period of 1 hour to 31.7 g (0.199 mole) of 4-carboethoxy oxazolidin-2-one dissolved in 300 ml of ethanol. During the addition the temperature rises from 15° C. to 30° C. The reaction solution is then stirred for 1 hour at room temperature.

The reaction solution is then hydrolysed with 30 g of ammonium chloride dissolved in 400 ml of water. The pH-value then amounts to pH 5. This solution is concentrated to dryness and repeatedly extracted by boiling with tetrahydrofuran. The tetrahydrofuran phases are combined and concentrated in a rotary evaporator. The pale yellow oil is dissolved in ethyl acetate. The crystals formed are filtered off under suction.

Yield: 23.4 g = 97% of the theoretical, m.p.: 77°–81° C.

(2) 4-Hydroxymethyl-4-methyl-5,5-pentamethylene oxazolidin-2-one 10.92 g (0.2882 mole) of sodium borohydride are added in portions over 1 hour to 59.5 g (0.262 mole) of 4-carbomethoxy-4-methyl-5,5-pentamethylene oxazolidin-2-one dissolved in 600 ml of ethanol. The reaction solution is then stirred for 12 hours at room temperature. It is then poured carefully into a saturated NH$_4$Cl-solution until the pH-value amounts to pH 5. This solution is repeatedly extracted with chloroform. The combined chloroform phases are dried over Na$_2$SO$_4$ and concentrated in a rotary evaporator. The pale yellow oil is taken up in ether. Crystals precipitate after a short time.

Yield: 43.0 g = 82.5% of the theoretical, m.p.: 113°–115° C.

(3) 4-(α-Hydroxybenzyl)-oxazolidin-2-one 3 g (15.8 mMole) of 4-benzoyl oxazolidin-2-one are dissolved in 100 ml of ethanol, followed by the addition in portions at room temperature of 900 mg (23.8 mMole) of sodium borohydride. The mixture is then stirred for 2.5 hours at room temperature. The reaction solution is then hydrolysed with a saturated ammonium chloride solution. The aqueous phase is repeatedly extracted with CHCl$_3$, the organic phases are combined, dried over Na$_2$SO$_4$ and concentrated in a rotary evaporator. The oil is taken up in methanol. The crystals are filtered under suction.

Yield: 2.2 g = 75% of the theoretical, m.p.: 130°–140° C.

(4) 4-(α-Hydroxy-p-chlorobenzyl)-oxazolidin-2-one 1 g (4.4 mMole) of 4-(p-chlorobenzoyl)-oxazolidin-2-one is dissolved in 50 ml of ethanol, followed by the addition in portions at room temperature of 300 mg (8.0 mMole) of sodium borohydride. After 1 hour, a saturated NH$_4$Cl-solution is added to the reaction solution which is then repeatedly extracted with chloroform. The combined organic phases are dried over Na$_2$SO$_4$ and concentrated. The yellow oil is taken up in ether/hexane. The crystals formed are filtered off under suction.

Yield: 0.5 g = 50% of the theoretical, m.p.: 126°–128° C.

(5) 4-[1-(1-Hydroxyethyl)]-5-phenyl oxazolidin-2-one 7.2 g (0.190 mole) of sodium borohydride are added in portions over a period of 1 hour to 3.8 g (0.018 mole) of 4-acetyl-5-phenyl oxazolidin-2-one dissolved in 50 ml of ethanol. The reaction solution is then stirred for 1 hour at room temperature, followed by the addition of a saturated ammonium chloride solution and repeated extraction with chloroform. The combined chloroform phases are dried and concentrated. The yellow oil is taken up in a little methanol. The crystals formed are filtered under suction.

Yield: 3 g = 78.5% of the theoretical, m.p.: 133°–134° C.

The following derivatives are produced in accordance with these Examples:

$$R_6-\overset{R_5}{\underset{\underset{\displaystyle C=O}{O}}{C}}-\overset{R_4}{\underset{\underset{\displaystyle N-R_1}{}}{C}}-\overset{R_3}{\underset{}{CH}}-OH$$

| Example No. | R$_1$ | R$_3$ | R$_4$ | R$_5$ | R$_6$ | m.p. °C. |
|---|---|---|---|---|---|---|
| 6 | H | H | CH$_3$ | CH$_3$ | C$_6$H$_5$ | 168–170 (ethanol) |
| 7 | H | H | H | C$_6$H$_5$ | C$_6$H$_5$ | 163–165 (ethyl acetate) |
| 8 | H | H | H | H | C$_6$H$_5$ | 103–105 (methanol/isopropyl ether) |
| 9 | H | H | H | CH$_3$ | C$_6$H$_5$ | 100–101 (ethyl acetate) |
| 10 | H | 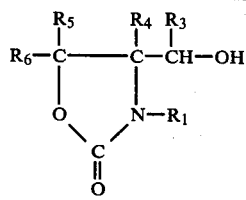—CH$_3$ | H | H | H | 105–107 (ether/hexane) |
| 11 | H | —⟨C$_6$H$_4$⟩—CH$_3$ | H | H | H | 117–119 (ether/petroleum ether) |

-continued

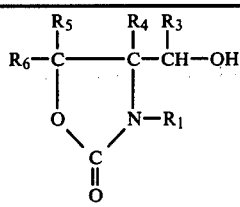

| Example No. | R₁ | R₃ | R₄ | R₅ | R₆ | m.p. °C. |
|---|---|---|---|---|---|---|
| 12 | H | CH₃ (2,4-dimethylphenyl) | H | H | H | 124–126 (isopropyl ether/hexane) |
| 13 | H | (3,4-dimethoxyphenyl) | H | H | H | 131–133 (methanol/isopropyl ether) |

EXAMPLES ILLUSTRATING THE APPLICATION OF GRIGNARD REACTIONS

(14) 4-[1-(1-n-Butyl-1-hydroxy)-n-pentyl]-5-phenyl oxazolidin-2-one 11.06 g (0.05 mole) of 4-carbomethoxy-5-phenyl oxazolidin-2-one dissolved in 100 ml of absolute tetrahydrofuran are slowly added dropwise to a Grignard solution prepared from 20.5 ml (0.2 mole) of n-butyl bromide in 50 ml of absolute ether and 4.86 g (0.2 gram equivalent) of Mg in 20 ml of absolute ether. The reaction temperature should not rise above +16° C. during the dropwise addition. When after 1 hour the tetrahydrofuran solution has been added, the reaction solution is stirred for another 1.5 hours at 30° C., subsequently hydrolysed with a saturated NH₄Cl-solution and repeatedly extracted with ether. The organic phases are combined and dried over Na₂SO₄. The solvent is distilled off. The residue becomes crystalline.

Yield: 7.1 g=46% of the theoretical, m.p.: 130°–132° C.

(15) 3-N-Methyl-4-[1-(1-hydroxy-1-methyl)-ethyl]-5,5-diphenyl oxazolidin-2-one 7.82 g (0.024 mole) of 3-N-methyl-4-carboethoxy-5,5-diphenyl oxazolidin-2-one dissolved in 200 ml of absolute tetrahydrofuran are slowly added dropwise under nitrogen to a Grignard solution prepared from 2.9 g (0.12 mole) of magnesium and 17 g (0.12 mole) of methyl iodide in 100 ml of absolute ether. The reaction temperature is in the range from 25° to 30° C. The reaction solution is then heated under reflux for 2 hours to boiling point. It is then hydrolysed with a saturated NH₄Cl-solution. The precipitated product is filtered off under suction.

Crude product: 7.64 g, m.p.: 195°–210° C.

This substance is recrystallised twice from ethanol.

Yield: 2.5 g=33.5% of the theoretical, m.p.: 215°–217° C.

(16) 4-[α-(Hydroxy-p-tolyl)-benzyl]-oxazolidin-2-one 5.0 g (26.2 mMole) of 4-benzoyl oxazolidin-2-one dissolved in 100 ml of absolute tetrahydrofuran are slowly added dropwise at 10° to 15° C. to a Grignard solution prepared from 9 ml (75.8 mMole) of p-chlorotoluene and 1.84 g (0.076 gram equivalents) of magnesium in 150 ml of absolute tetrahydrofuran. The reaction solution is then stirred for 1 hour at room temperature, hydrolysed with ice-ammonium chloride and repeatedly extracted with ether. The combined organic phases are dried over Na₂SO₄ and concentrated. The pale yellow oil is taken up in isopropanol/isopropyl ether. The crystals formed are filtered off under suction.

Yield: 2.5 g=35.3% of the theoretical, m.p.: 216°–218° C.

(17) 4-[α-(Hydroxy cyclohexyl)-benzyl]-oxazolidin-2-one 5.0 g (0.0262 mole) of 4-benzoyl oxazolidin-2-one dissolved in 100 ml of absolute tetrahydrofuran are added dropwise while cooling with ice to a Grignard solution prepared from 12.8 ml (0.127 mole) of bromocyclohexane and 2.98 g (0.128 gram equivalent) of magnesium in 150 ml of absolute tetrahydrofuran. This solution is stirred for 2 hours at 60° C., subsequently hydrolysed with approximately 500 ml of a saturated ammonium chloride solution and repeatedly extracted with chloroform. The organic phases are combined, dried over Na₂SO₄ and concentrated in a rotary evaporator. The oil is taken up in ether. The crystals formed are filtered off under suction.

Yield: 2.5 g=35% of the theoretical, m.p.: 190°–192° C.

(18) 4-[1-(1-Hydroxy-1-phenyl)-propyl]-5-methyl oxazolidin-2-one 10.26 g (0.05 mole) of 4-benzoyl-5-methyl oxazolidin-2-one dissolved in 250 ml of absolute tetrahydrofuran are added dropwise under nitrogen while cooling with ice to a Grignard solution prepared from 7.30 g (0.3 gram equivalent) of magnesium and 35.96 g (0.33 mole) of ethyl bromide in 120 ml of absolute ether. The internal temperature rises from +2° C. to +12° C. The reaction solution is then heated under reflux for 1 hour to boiling point, hydrolysed with a saturated ammonium chloride solution and repeatedly extracted with ether. The organic phases are combined, dried and concentrated. 12.85 g of a solid residue are obtained, being recrystallised from 60 ml of methanol.

Yield: 8.3 g=70% of the theoretical, m.p.: 192°–194° C.

The derivatives listed in Table 2 below were similarly prepared.

Table 2

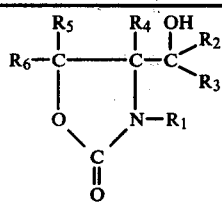

| Example No. | $R_1$ | $R_2$ | $R_3$ | $R_4$ | $R_5$ | $R_6$ | M.p. °C. |
|---|---|---|---|---|---|---|---|
| 19 | H | $C_6H_5-$ | $C_6H_5-$ | H | H | H | 205–207 (methanol/ether) |
| 20 | H | $m\text{-}Cl-C_6H_4-$ | $m\text{-}Cl-C_6H_4-$ | H | H | H | 173–174 (methanol) |
| 21 | H | $o\text{-}CH_3O-C_6H_4-$ | $o\text{-}CH_3O-C_6H_4-$ | H | H | H | 172–173 (benzene) |
| 22 | H | $m\text{-}CH_3O-C_6H_4-$ | $m\text{-}CH_3O-C_6H_4-$ | H | H | H | 134–135 (benzene) |
| 23 | H | $p\text{-}CH_3O-C_6H_4-$ | $p\text{-}CH_3O-C_6H_4-$ | H | H | H | 118–120 (benzene) |
| 24 | H | $o\text{-}CH_3-C_6H_4-$ | $o\text{-}CH_3-C_6H_4-$ | H | H | H | 208–210 (methanol/ether) |
| 25 | H | $m\text{-}CF_3-C_6H_4-$ | $m\text{-}CF_3-C_6H_4-$ | H | H | H | 178–180 (ether/isopropanol) |
| 26 | H | $m\text{-}F-C_6H_4-$ | $m\text{-}F-C_6H_4-$ | H | H | H | 184–186 (ether) |
| 27 | H | $-CH_2-C_6H_5$ | $-CH_2-C_6H_5$ | H | H | H | 173–174 (methanol/isopropyl ether) |
| 28 | H | $-CH_2-\text{C}_6\text{H}_4-Cl$ | $-CH_2-\text{C}_6\text{H}_4-Cl$ | H | H | H | 163–165 (methanol) |
| 29 | H | $-CH_2-CH=CH_2$ | $-CH_2-CH=CH_2$ | H | H | H | 96–97 (methanol/isopropyl ether) |
| 30 | H | $C_6H_5-$ | $C_6H_5-$ | H | H | $-CH_3$ | 215–217 (methanol) |
| 31 | H | $m\text{-}Cl-C_6H_4-$ | $m\text{-}Cl-C_6H_4-$ | H | H | $-CH_3$ | 220–221 (isopropyl ether) |
| 32 | H | $-CH_2-C_6H_5$ | $-CH_2-C_6H_5$ | H | H | $-CH_3$ | 93–94 (isopropyl ether) |
| 33 | H | $-CH_2-\text{C}_6\text{H}_4-Cl$ | $-CH_2-\text{C}_6\text{H}_4-Cl$ | H | H | $-CH_3$ | 100–101 (isopropyl ether) |
| 34 | H | $-CH_2-CH=CH_2$ | $-CH_2-CH=CH_2$ | H | H | $-CH_3$ | 90–91 (isopropyl ether) |
| 35 | H | $-C_2H_5$ | $-C_2H_5$ | H | H | $-CH_3$ | 69–70 (isopropyl ether) |
| 36 | H | $n\text{-}C_4H_9-$ | $n\text{-}C_4H_9-$ | H | H | $-CH_3$ | 118–119 (isopropyl ether) |
| 37 | H | $-CH_3$ | $-CH_3$ | H | H | $-C_6H_5$ | 203–204 (methanol/ether) |
| 38 | $-CH_3$ | $-CH_3$ | $-CH_3$ | H | H | $-C_6H_5$ | 100–101 (acetic acid-n-butyl ester) |
| 39 | $-CH_2-CH=CH_2$ | $-CH_3$ | $-CH_3$ | H | H | $-C_6H_5$ | 92–93 (acetic acid-n-butyl ester) |
| 40 | H | $-C_2H_5$ | $-C_2H_5$ | H | H | $-C_6H_5$ | 160–161 (methanol) |
| 41 | H | $n\text{-}C_3H_7-$ | $n\text{-}C_3H_7-$ | H | H | $-C_6H_5$ | 136–138 (ether) |
| 42 | H | $-C_6H_5$ | $-C_6H_5$ | H | H | $-C_6H_5$ | 238–239 (methanol) |
| 43 | H | $-CH_2-CH=CH_2$ | $-CH_2-CH=CH_2$ | H | H | $-C_6H_5$ | 115–117 (isopropanol) |
| 44 | H | $C_2H_5$ | $-C_2H_5$ | H | H | H | 106–107 (methanol/isopropyl ether) |
| 45 | H | $n\text{-}C_3H_7-$ | $n\text{-}C_3H_7-$ | H | H | H | 120–121 (ether) |
| 46 | $-CH_2-C_6H_5$ | $-CH_3$ | $-CH_3$ | H | H | $-C_6H_5$ | 90–91 (ethyl acetate) |
| 47 | H | $-CH_3$ | $-CH_3$ | H | $-C_6H_5$ | $-C_6H_5$ | 239–240 (ethanol) |
| 48 | H | $-CH_2CH=CH_2$ | $-CH_2-CH=CH_2$ | H | $-C_6H_5$ | $-C_6H_5$ | 138–139 (ether) |
| 49 | H | $m\text{-}Cl-C_6H_4-$ | $-C_6H_5$ | H | H | H | 155–157 (ether) |
| 50 | H | $p\text{-}Cl-C_6H_4-$ | $-C_6H_5$ | H | H | H | 116–118 (isopropylether/isopropanol) |
| 51 | H | $m\text{-}CF_3-C_6H_4-$ | $-C_6H_5$ | H | H | H | 151–153 |

Table 2-continued

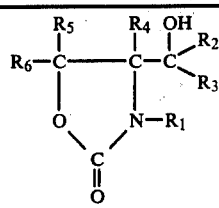

| Example No. | $R_1$ | $R_2$ | $R_3$ | $R_4$ | $R_5$ | $R_6$ | M.p. °C. |
|---|---|---|---|---|---|---|---|
| | | | | | | | (hexane/ether) |
| 52 | H | o-Cl—$C_6H_4$— | —$C_6H_5$ | H | H | H | 195–197 (benzene) |
| 53 | H | m-F—$C_6H_4$— | —$C_6H_5$ | H | H | H | 189–191 (benzene) |
| 54 | H | —$C_2H_5$ | —$C_6H_5$ | H | H | H | 192–195 (ether/hexane) |
| 55 | H | —$CH_2$—$C_6H_5$ | p-$CH_3$—$C_6H_4$— | H | H | H | 168–171 (ether) |
| 56 | H | —$CH_2$—$C_6H_5$ | —$C_6H_5$ | H | H | H | 199–203 (ether) |
| 57 | H | o-$CH_3$—O—$C_6H_4$— | —$C_6H_5$ | H | H | H | 174–176 (ether) |
| 58 | H | —$CH_2$—CH=$CH_2$ | —$C_6H_5$ | H | H | H | 112–113 (methanol) |
| 59 | H | —$CH_3$ | —C H -p-Cl | H | H | H | 115–118 (ether) |
| 60 | H | —$C_2H_5$ | —$C_6H_4$-p-Cl | H | H | H | 176–179 (methanol/ether) |
| 61 | H | —$CH_3$ | —$C_6H_5$ | H | H | H | 198–200 (methanol) |
| 62 | H | —$C_2H_5$ | -C6H3(CH3)2 (3,4-dimethylphenyl) | H | H | H | 184–186 (methanol/ether) |
| 63 | H | —$C_2H_5$ | -C6H3(OCH3)2 | H | H | H | 108–110 (methanol) |
| 64 | —$CH_3$ | —$C_2H_5$ | —$C_6H_5$ | H | H | H | 172–173 (methanol/isopropyl ether) |
| 65 | H | n-$C_3H_7$— | —$C_6H_5$ | H | H | H | 172–173 (methanol/isopropyl ether) |
| 66 | H | —$CH_3$ | n-$C_4H_9$— | H | —$C_6H_5$ | H | 160–161 (benzene/isopropyl ether) |

EXAMPLES ILLUSTRATING THE OPTIONAL REACTION WITH A HALOGENATING AGENT

(67) 4-Chloromethyl-5-methyl-5-phenyl oxazolidin-2-one 1.5 ml (10 mMole) of thionyl chloride are slowly added dropwise at 0° to +5° C. to 1.04 g (5 mMole) of 4-hydroxymethyl-5-methyl-5-phenyl oxazolidin-2-one dissolved in 15 ml of pyridine. After 1 hour at 50° C., the reaction solution is stirred overnight at room temperature, poured onto ice and repeatedly extracted with chloroform. The combined chloroform phases dried over $Na_2SO_4$ are concentrated. The crystals formed are recrystallised from methanol.

Yield: 0.56 g=50% of the theoretical, m.p.: 150°–152° C.

The derivatives listed in Table 3 below were similarly prepared.

Table 3

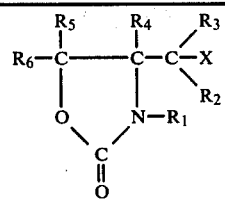

| Example No. | X | $R_1$ | $R_2$ | $R_3$ | $R_4$ | $R_5$ | $R_6$ | m.p. °C. |
|---|---|---|---|---|---|---|---|---|
| 68 | Cl | H | —$C_2H_5$ | —$C_6H_5$ | H | H | H | 170–172 (benzene) |
| 69 | Cl | H | H | H | H | H | H | oil, B.p. 140° C./0.02 Torr |
| 70 | Cl | H | H | H | —$CH_3$ | —$(CH_2)_5$— | | 175–180 (methanol) |
| 71 | Cl | H | H | H | H | —$C_6H_5$ | —$C_6H_5$ | 200–202 (ethanol) |

Table 3-continued

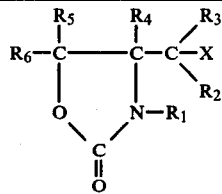

| Example No. | X | $R_1$ | $R_2$ | $R_3$ | $R_4$ | $R_5$ | $R_6$ | m.p. °C. |
|---|---|---|---|---|---|---|---|---|
| 72 | Cl | H | H | H | H | $-C_6H_5$ | H | 126–128 (methanol) |
| 73 | Br | H | H | H | H | $-C_6H_5$ | H | 117–118 (methanol) |
| 74 | Br | H | H | H | H | H | H | 65–68 (ethyl acetate/petroleum ether) |

PRACTICAL EXAMPLES

EXAMPLE 75

A tablet consists of 100 mg of the compound according to Example 33, 10 mg of tragacanth, 147.5 mg of lactose, 25 mg of corn starch, 15 mg of talcum and 2.5 mg of magnesium stearate. The active principle is granulated with the lactose mixture in the usual way, magnesium stearate is added and the mixture is pressed into tablets in the usual way.

EXAMPLE 76

A dragee consists of 20 mg of the compound of Example 27, 110 mg of lactose, 25 mg of Avicel and 5 mg of talcum. The constituents are mixed and the mixture pressed in the usual way into tablets 8 mm in diameter and weighing 160 mg. The tablets are then coated with sugar syrup to a weight of 250 mg.

EXAMPLE 77

A capsule consists of 300 mg of the compound of Example 67 and 10 mg of talcum. The active principle is mixed with the talcum mixture and hard gelatin capsules filled with the resulting mixture.

EXAMPLE 78

A suspension consists of 1.0 g of the compound of Example 27, 2.0 g of bentonite, 1.5 g of sodium carboxymethyl cellulose, 30 g of sugar, 0.3 g of potassium sorbate and 0.01 g of peppermint aroma. The finely ground active principle is mixed with the above-mentioned excipients and a suspension 100.0 g in weight is prepared in the usual way by adding water. The individual dose amounts to between 1 and 3 teaspoons full.

EXAMPLE 79

A solution suitable for intravenous administration contains 5% by weight of the compound of Example 33, the quantity of sodium chloride required for forming an isotonic solution, 10 to 20% by weight of ethanol, 15 to 25% by weight of propylene glycol and 15 to 75% by weight of water suitable for injection.

EXAMPLE 80

A tablet produced in accordance with Example 75 consisting of 50 mg. of the active compound according to Example 43 and the equivalent amount of the other ingredients was administered to a human suffering from motor restlessness. Within a period of several minutes the patient reported a muscle relaxing, tiring and ataraktic sedation. Studies of an electroencephalogram showed the characteristic signs of a sedation with a decrease of effectiveness in the alpha and beta band and a change of the range of main activity to the lower frequency range. Indications of a shallow sleep phase clearly increased in the electroencephalogram registered 5 hours after administration of the drug.

We claim:

1. 4-[1'(1'-Hydroxy-1'-methyl)-ethyl]-5-phenyl oxazolidin-2-one corresponding to the formula

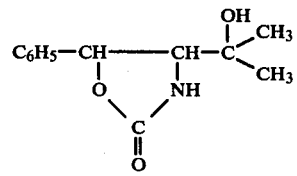

* * * * *

UNITED STATES PATENT OFFICE
CERTIFICATE OF CORRECTION

PATENT NO. : 4,179,442
DATED : December 18, 1979
INVENTOR(S) : Kollensperger et al.

It is certified that error appears in the above-identified patent and that said Letters Patent are hereby corrected as shown below:

In Table 1a, Example No. 38, $R_1$ Substituent Column,

"3" should read -- $-CH_3$ --.

Signed and Sealed this

First Day of July 1980

[SEAL]

Attest:

SIDNEY A. DIAMOND

Attesting Officer — Commissioner of Patents and Trademarks